United States Patent [19]
Grevis et al.

[11] Patent Number: 4,940,054
[45] Date of Patent: Jul. 10, 1990

[54] APPARATUS AND METHOD FOR CONTROLLING MULTIPLE SENSITIVITIES IN ARRHYTHMIA CONTROL SYSTEM INCLUDING POST THERAPY PACKING DELAY

[75] Inventors: Richard Grevis, Rose Bay, Australia; Norma L. Gilli, Littletown, Colo.

[73] Assignee: Telectronics N.V., Curacao, Netherlands Antilles

[21] Appl. No.: 187,797

[22] Filed: Apr. 29, 1988

[51] Int. Cl.$^5$ .............................................. A61N 1/00
[52] U.S. Cl. ............................................. 128/419 PG
[58] Field of Search ......... 128/419 PT, 419 P, 419 D, 128/419 PG

[56] References Cited

U.S. PATENT DOCUMENTS

| | | | |
|---|---|---|---|
| 3,952,750 | 4/1976 | Mirowski et al. | 128/419 D |
| 4,184,493 | 1/1980 | Langer et al. | 128/419 D |
| 4,393,877 | 7/1983 | Imran et al. | 128/419 D |
| 4,554,920 | 11/1985 | Baker, Jr. et al. | 128/419 PG |
| 4,574,437 | 3/1986 | Segerstad et al. | 128/419 PG |
| 4,593,695 | 6/1986 | Wittkampf | 128/419 PG |
| 4,712,556 | 12/1987 | Baker, Jr. | 128/419 PG |

OTHER PUBLICATIONS

Roger A. Winkle et al., "The Automatic Implantable Defibrillator: Local Ventricular Bipolar Sensing to Detect Ventricular Tachycardia and Fibrillation", The Amer. Journal of Cardiology, vol. 52, pp. 265–270 (1983).

*Primary Examiner*—Francis Jaworski
*Assistant Examiner*—George Manuel
*Attorney, Agent, or Firm*—Gottlieb, Rackman & Reisman

[57] ABSTRACT

An apparatus and method for tachyarrhythmia reversion uses multiple sensitivities programmed for automatic operation. A first (medium) sensitivity is used normally for the detection of sinus rhythm and ventricular tachycardia. A second (higher) sensitivity is designed for differentiating ventricular fibrillation from asystole. A third (lower) sensitivity can also be programmed into the device to differentiate between R-waves and high amplitude current of injury T-waves which may occur post shock. Following the delivery of antitachycardia therapy in the form of either antitachycardia pacing therapy or cardioversion shock therapy, there is a pause, or post therapy pacing delay for a period of time prior to the commencement of bradycardia support pacing. The magnitude of the delay period is substantially greater than the normal bradycardia support pacing standby interval.

39 Claims, 7 Drawing Sheets

APPARATUS AND METHOD FOR CONTROLLING MULTIPLE SENSITIVITIES IN ARRHYTHMIA CONTROL SYSTEM INCLUDING POST THERAPY PACKING DELAY

TECHNICAL FIELD

This invention relates to implantable medical devices which monitor the cardiac state of a patient by sensing sinus rhythm, ventricular tachycardia and ventricular fibrillation and which deliver therapy in the form of electrical energy to cardiac tissue to revert tachycardia and restore sinus rhythm.

As used herein antitachycardia pacing refers to any pacing for the reversion of tachycardia. The term tachyarrhythmia refers to any fast abnormal rhythm of the heart which may be amenable to treatment by electrical discharges. This specifically includes ventricular tachycardia (VT), supraventricular tachycardia (SVT), ventricular flutter, ventricular fibrillation (VF), atrial tachycardia (AT), atrial flutter and atrial fibrillation (AF).

The term therapy as used herein includes the processes used between the detection and the reversion of a tachyarrhythmia and includes the actions of antitachycardia pacing, cardioversion and/or defibrillation shocks. The term cardioversion refers to the discharge of electrical energy into the cardiac tissue in an attempt to terminate or revert a tachyarrhythmia. This may take the form of a high energy discharge (up to 40 Joules or more) or a low energy discharge (less than 1 Joule). Cardioversion shocks may or may not be synchronized to the rhythm of the heart. Defibrillation is a particular example of cardioversion.

This invention applies equally to devices which deliver energy synchronized to an R-wave and to those that do not, and it applies to devices which use lower energy pulses as well as to devices which use higher energy pulses. The invention applies to devices which deliver cardioverting shocks alone as well as to devices which deliver antitachycardia pacing pulses alone or in combination with cardioverting shocks. The invention will usually apply to implantable ventricular cardioverters, but is equally applicable to atrial cardioverters or multiple chamber cardioverters or defibrillators. The invention applies also to the delivery of any antitachycardia pacing pulses and post reversion pacing therapy.

In general, the invention applies to a tachyarrhythmia reversion device programmed for the use of multiple sensitivities during its normal automatic operation. A first sensitivity level detects sinus and VT/VF's while a second (higher) sensitivity level differentiates between low amplitude VF's and asystole. A third (lower) sensitivity level may also be programmed into the device to differentiate between R-waves and high amplitude current of injury T-waves which may occur post shock

BACKGROUND ART

An example of an implantable cardioverting device is in Pat. No. 3,952,750 to Mirowski et al This device uses an AGC (Automatic Gain Control) for sensitivity adjustment. An analog signal is used as a basis for adjustment Signal averaging is performed on peak amplitudes and the sensitivity threshold is automatically adjusted by this process. However, this device does not perform any bradycardia support and was designed to detect VF (ventricular fibrillation) only. That is, it was not designed for detection of both VF and sinus rhythm and does not operate effectively as a detection device for bradycardia support and normal sinus rhythm A problem also exists in AGC devices where a VF has a variable amplitude The presence of occasional peaks in its waveform in addition to lower "sub threshold" amplitudes is known to automatically adjust on the basis of the peaks with the effect of ignoring the lower amplitudes of the waveform, hence producing an erroneous result. Thus, an incorrect sensitivity adjustment is performed. VF is therefore undetected and could be mistaken for sinus rhythm This may cause severe difficulties, discomfort and may even cause the death of the patient.

If all VF signals were low peak, the AGC would give a correct result, but it does not allow for the existence of occasional high peaks. Thus the device could erroneously operate on the basis that sinus rhythm had been restored. A further problem with AGC devices is that they fail to detect rapidly changing amplitudes which are often observed during VF.

Furthermore, AGC devices are not generally designed to cope with bradycardia support or the condition of asystole.

If there is no signal response and asystole is present, an AGC device could automatically increase detector sensitivity until unwanted noise signals are picked up, such as muscle noise, electrical noise, etc., and these could be recognized by the device as being an arrhythmia The device would then cause the application of incorrect therapy, causing great discomfort and possibly death of a patient. This is a reason why the device has not generally been implanted in patients suffering from the effects of asystole and who need a device designed for bradycardia support.

As a result of these shortcomings, an AGC has not been effective in detection in implantable devices in patients who suffer from asystole and require bradycardia support, in addition to antitachyarrhythmia therapy In addition to antitachyarrhythmia devices, there are some existing pacemaker devices which include an AGC for sensitivity adjustments. These pacemaker devices may be effective in organized heart rhythm detection, but are not designed to allow for VF detection or for differentiation between VF and asystole.

Another prior art detection device is described in U.S. Pat. No. 4,184,493 to Langer et al and relates to VF detection using the principle of a probability-density function. In this device, the ECG is filtered by a high pass filter after which the filtered ECG is used to derive the control voltage for an automatic gain control circuit. However, this device does not overcome the problem of detection of lower amplitude or fine VF's due to the high pass filtering of the VF signal Furthermore, the device is not designed for bradycardia support of patients experiencing asystole An article in "The American Journal of Cardiology" Vol. 52, page 265, entitled "The Automatic Implantable Defibrillator: Local Ventricular Bipolar Sensing to Detect Ventricular Tachycardia and Fibrillation" by Winkle et al. refers at page 270 to the use of rate detection circuits in conjunction with a morphology dependent criterion, such as the probability-density function to minimize the possibility of delivery of shocks during sinus or other narrow-QRS SVT. The article then states that the "addition of a morphology-dependent criterion is done at the expense of increasing the likelihood that some VT's will not be recognized by the system" and that the device "may occasionally deliver a shock for a a sinus or other SVT". This further emphasizes the need for a device which reliably detects VT and sinus rhythm and is also designed for bradycardia support pacing Another prior art heart rate detection device is shown in U.S. Pat. No. 4,393,877 to Imran. This heart rate detection apparatus includes two mutually inclusive detector circuits responsive to ECG waveforms of different characteristics. One detection circuit is responsive to ECG waves with high slew rates, or spiky waves, while the other detection circuit is responsive to ECG waves with low slew rates, or sinusoidal waves. This device, however, is not designed to distinguish between low amplitude VF and asystole. Also the device is not designed to overcome the problem of double sensing after a defibrillation shock due to far-field R-waves or current of injury T-waves which may occur, for example when, post shock, the T-wave is, for a period of time, of a higher amplitude than the R-wave.

Furthermore, some attempts have been made at permanently increasing the sensitivity to overcome the problem of loss of low amplitude VF signals. This has resulted in the additional problem of double-sensing of VT and sinus rhythm signals, causing erroneous results in the detection device which can produce an incorrect therapy, causing great discomfort and possibly patient death.

Another problem with existing detection devices can be caused by the presence of a current of injury T-wave. It is known that after therapy (shock or pacing) when a tachyarrhythmia has been reverted and sinus rhythm has been restored, the T-wave has, for a time, an amplitude which may be as high as or higher than that of the R-wave, thereby causing a double counting effect Hence there may be at times a need in antitachyarrhythmia devices to differentiate between R-waves and current of injury T-waves in initial post therapy sinus rhythm.

DISCLOSURE OF THE INVENTION

It is a principal object of the present invention to provide a method and apparatus for controlling the sensitivity of an electogram detection channel so that a detector can distinguish between sinus rhythm and ventricular tachycardia.

It is a further object of the invention to provide a method and apparatus for controlling sensitivity so that a detector can distinguish between ventricular tachycardia and asystole.

The problems of prior art detection devices are overcome by our invention which provides a device for the reliable detection of VT and sinus along with the ability to provide bradycardia support pacing. In addition, our invention provides a device which accurately differentiates between asystole and fine VF's. Furthermore, the invention has the capability of differentiating between R-waves and current of injury T-waves in initial post-therapy sinus.

The invention provides a heart monitoring device with multiple sensitivities as programmable parameters. The device includes a medium sensitivity which detects sinus and VT/VF's while a higher sensitivity differentiates between fine VS's and asystole The device may be programmed to include a third (low) sensitivity to prevent double sensing after a defibrillation shock or pacing by distinguishing between the R-wave and a current of injury T-wave.

According to the invention, there is provided a medical device for treating tachyarrhythmias comprising means for sensing the presence of a patient tachyarrhythmia, means for delivering antitachyarrhythmia therapy, and means for programming at least two sensitivity levels. The device has signal output means corresponding to each of the sensitivity levels, whereby a first sensitivity level is for normal sensing of sinus rhythm, VF and VT, and a second sensitivity level being higher than the first sensitivity level is for differentiating low amplitude VF from asystole. The device includes a means for switching from the first sensitivity level to the second sensitivity level when there is an absence of signal output at the first sensitivity level. The device includes means for switching back to the first sensitivity level following the delivery of antitachyarrhythmia therapy, a sensed sinus rhythm event or a paced event.

According to the invention, a method of sensing in a tachyarrhythmia reversion device comprises the steps of programming two sensitivities into the device whereby the first sensitivity is for detecting sinus and VT and the second sensitivity is higher than the first sensitivity, both sensitivities being capable of producing a corresponding signal output, switching over from the first sensitivity to the second sensitivity after the detection of a tachyarrhythmia and the disappearance of said signal output corresponding to the first sensitivity, and switching back from the second sensitivity to the first sensitivity upon completion of antitachyarrhythmia therapy.

BRIEF DESCRIPTION OF THE DRAWINGS

Further objects, features and advantages of the invention will become apparent upon consideration of the following detailed description in conjunction with the drawings, in which.

BEST MODE FOR CARRYING OUT THE INVENTION

Figure 1:
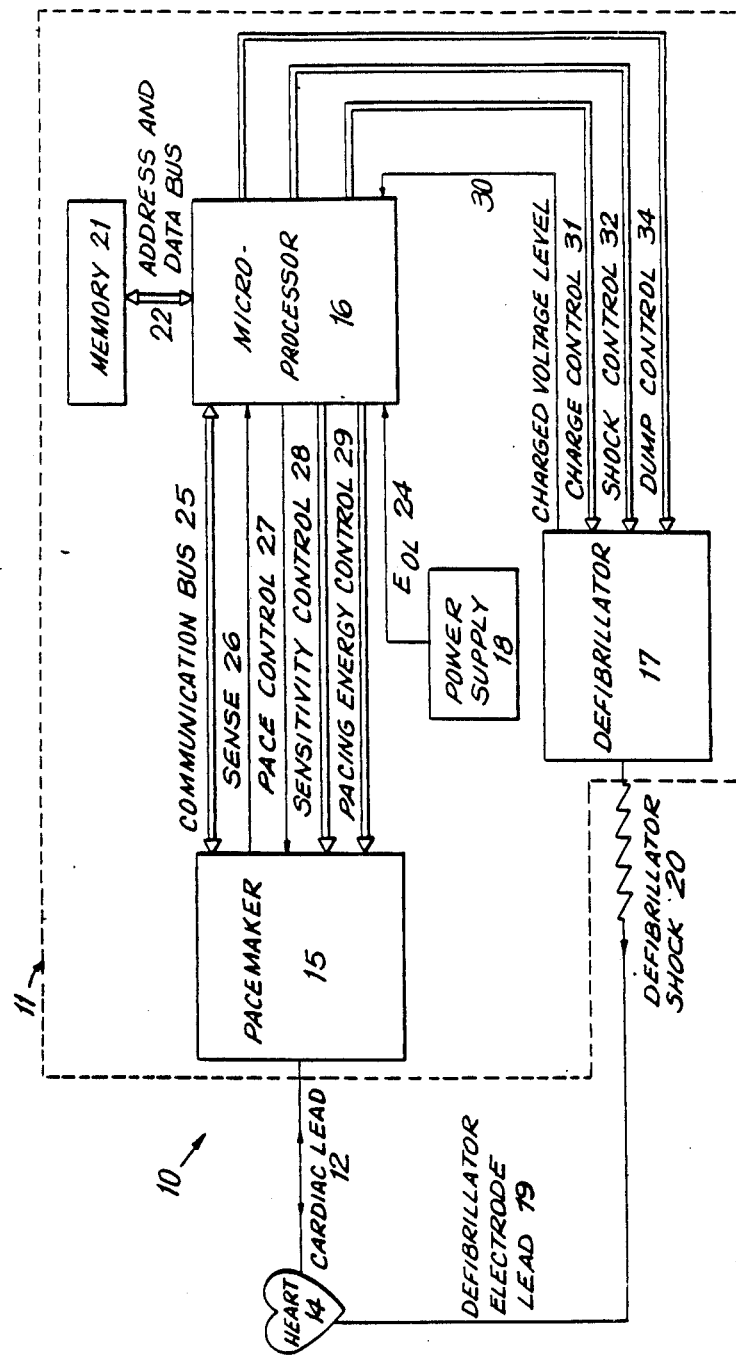
FIG. 1 is a block diagram of an arrhythmia control system in which the present invention may be used.

Referring to FIG. 1, there is depicted a block diagram of an arrhythmia control system 10. System 10 is designed to be implantable and includes a pulse module 11 and appropriate leads. More particularly, system 10 will generally include a cardiac lead extending to the atrium of a patient's heart for the administration of therapy to the atrium or a cardiac lead 12 extending to the ventricle of a patient's heart 14 for the administration of therapy to the ventricle. System 10 generally also includes a pacemaker 15 for the detection of analog signals representing cardiac electrical activity and for the delivery of pacing pulses to the heart; a microprocessor 16 which, in response to various inputs received from the pacemaker 15 as well as from a defibrillator 17, performs various operations so as to generate different control and data outputs to both pacemaker 15 and defibrillator 17; and a power supply 18 for the provision of a reliable voltage level to pacemaker 15, microprocessor 16 and defibrillator 17 by suitable electrical conductors (not shown). Defibrillator 17 produces a high voltage to charge its capacitors and then discharges them in response to control signals from microprocessor 16. A defibrillator electrode lead 19 transfers the energy of a defibrillator shock 20 from the implanted pulse module to the surface of the heart 14.

Microprocessor 16 is connected to an external memory 21 by an address and data bus 22. An end-of-life (EOL) signal line 24 is used to provide, to microprocessor 16, a logic signal indicative of the approach of battery failure in power supply 18.

As more fully described below, microprocessor 16 and pacemaker 15 are connected by a communication bus 25, a sense line 26, a pace control line 27, a sensitivity control bus 28, and a pacing energy control 29. As also more fully described below, microprocessor 16 is connected to defibrillator 17 by a charge level line 30, a charge control bus 31, a shock control bus 32, and a dump control bus 34.

Figure 2:
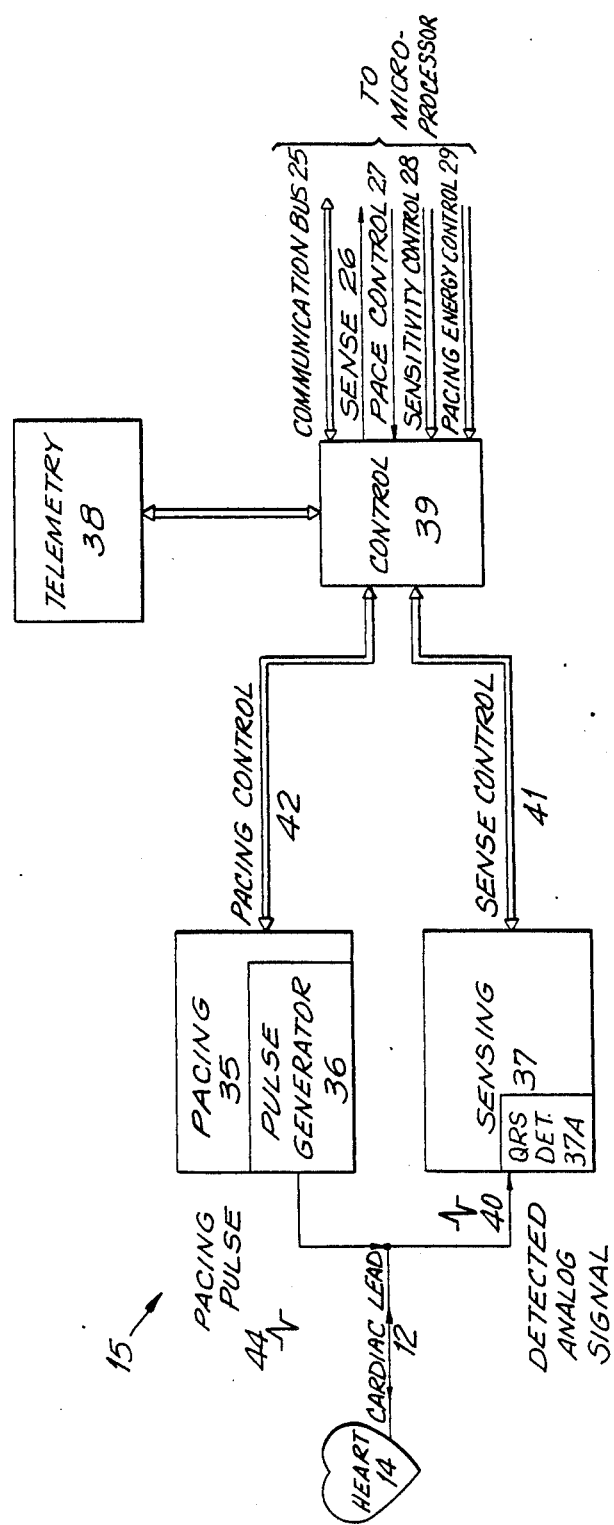
FIG. 2 is a block diagram of the pacemaker of FIG. 1.

Referring to FIG. 2, pacemaker 15 comprises pacing circuit 35 which includes a pacing pulse generator 36, sensing circuit 37, and telemetry circuit 38. In addition, there is a control block 39 which includes an interface to microprocessor 16.

In operation, sensing circuit 37 detects analog signals 40 from the heart 14 in an internal QRS detector 37A and converts the detected signals to digital signals. Furthermore, sensing circuit 37 receives an input sense control signal (which determines the sensitivity of the detection circuits in sensing circuit 37) by way of a sense control bus 41 from control block 39. As more fully described below, a change in this sensitivity will affect the voltage deviation required at the sensing electrode for a sense to be registered.

Pacing circuit 35 also receives inputs from control block 39 including a pace control and a pacing energy control by way of pacing control bus 42 which carries the signals on pace control line 27 and pacing energy control bus 29. The pace control determines the type of pacing to occur while the magnitude of the pulse energy is determined by the pacing energy control. Pacing circuit 35 causes pulse generator 36 to generate the pacing pulse 44 which is delivered to the patient's heart 14 by means of cardiac lead 12.

Telemetry circuit 38 provides a bi-directional link between control block 39 of pacemaker 15 and an external device such as a programmer. It allows data such as the operating parameters to be read from or altered in the implanted pulse module 11.

Figure 3:
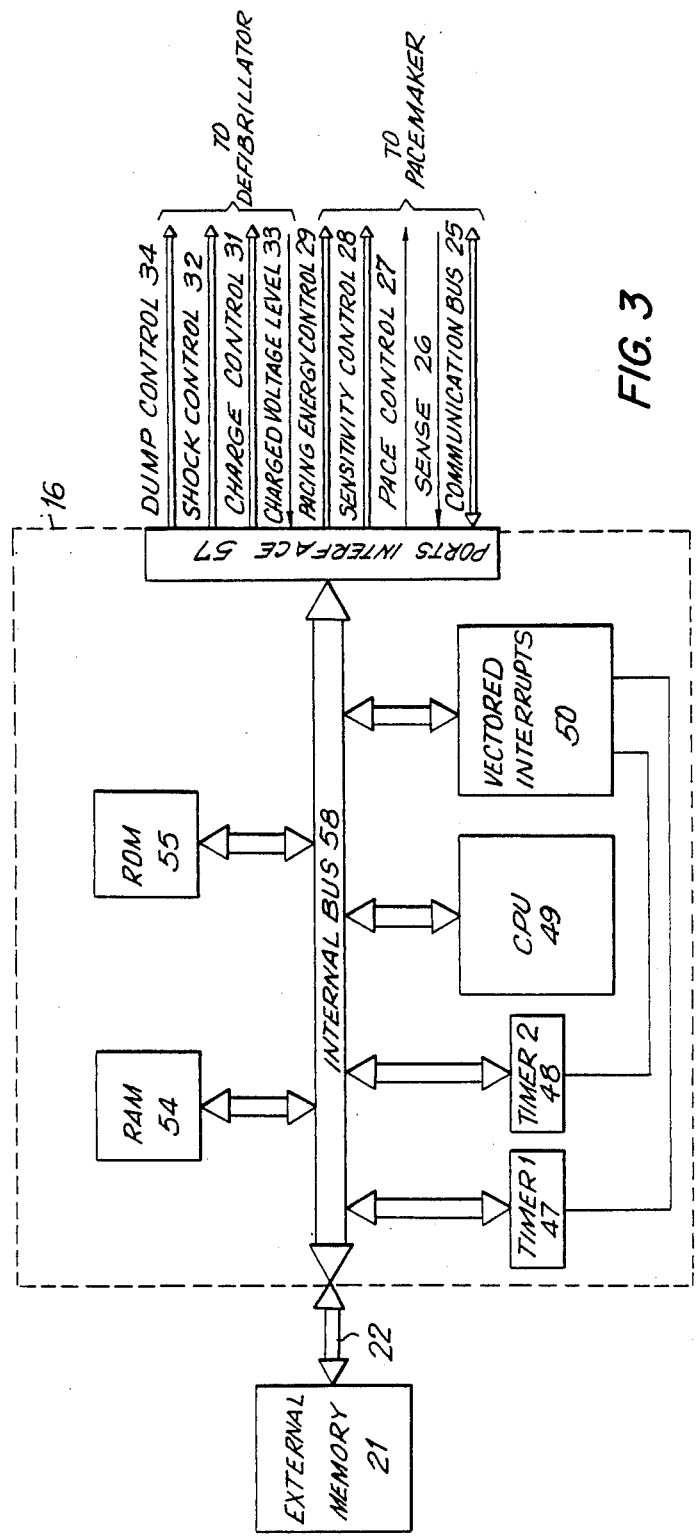
FIG. 3 is a block diagram of the microprocessor of FIG. 1.

Referring to FIG. 3, microprocessor 16 comprises two 16-bit timers 47 and 48, CPU 49, vectored interrupt block 50, RAM 54, ROM 55, ports interface 57 and an internal communications bus 58. RAM 54 acts as a scratch pad and active memory during execution of various programs stored in ROM 55 and used by microprocessor 16. These programs include system supervisory programs, detection algorithms for detecting various arrhythmias, and programming implementing the logic flow diagram of FIG. 4, as well as storage programs for storing, in external memory 21, data concerning the functioning of module 11 and the electrogram provided by cardiac lead 12. Timers 47 and 48 and associated control software implement some timing functions required by microprocessor 16 without resort entirely to software, thus reducing computational loads on and power dissipation by CPU 49.

Signals received from telemetry circuit 38 permit an external programmer (not shown) to change the operating parameters of pacemaker 15 by supplying appropriate signals to control block 39. Communications bus 25 serves to provide signals indicative of such control to microprocessor 16. Thus, it is also possible for an external programmer to control operation of defibrillator 17 by means of signals provided to microprocessor 16.

Appropriate telemetry commands may cause telemetry circuit 38 to transmit data to the external programmer. Data stored is read out, by microprocessor 16, on to communications bus 25, through control block 39 in pacemaker 15, and into control block 38 for transmission to the external programmer by a transmitter in telemetry circuit 38.

Microprocessor 16 receives various status and/or control inputs from pacemaker 15 and defibrillator 17. During normal pacer operations the input signal to pacemaker 15 is a sense signal on sense line 26 which is used by microprocessor 16 to perform operations such as arrhythmia detection. Microprocessor 16 produces outputs such as the pace control on pace control line 27 which determines the type of pacing to take place. Other pacemaker control outputs generated by microprocessor 16 include a pacing energy control signal on pacing energy control bus 29 which determines the magnitude of the pulse energy, and a sensitivity control signal on sensitivity control bus 28, which determines the sensitivity setting of the sensing circuit.

Microprocessor 16 provides to defibrillator 17 a shock control signal on shock control line 32 which indicates that a shock is to be delivered to the patient, a dump control signal on dump control line 34 which indicates that a shock is to be dumped at an internal load within defibrillator 17, and a charge control signal on charge control bus 31 which determines the voltage level of the shock to be delivered. Charge voltage level line 30 provides a digital signal representative of charge voltage from an analog to digital converter within defibrillator 17, thus providing a feedback loop which assures that a shock of proper energy level is delivered by defibrillator 17.

Figure 4:
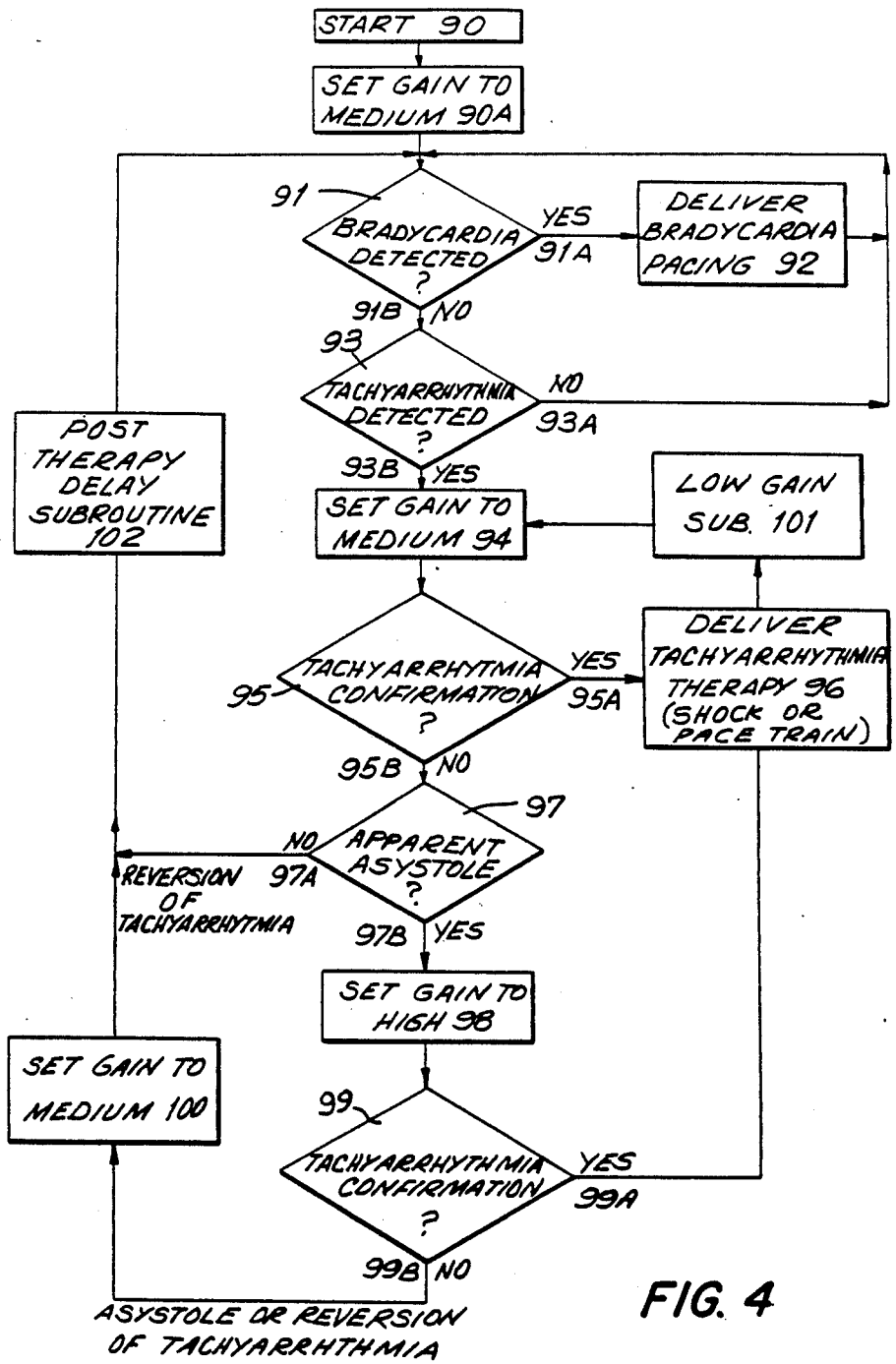
FIG. 4 is a logic flow diagram of the software executed by the microprocessor of FIG. 3 in accordance with the invention.

FIG. 4 is a logic diagram of the microprocessor flow control for controlling the sensitivity of sensing circuit 37, with the start being shown at 90. At 90A, the sensitivity is set to medium gain. At 91, a determination is made as to whether bradycardia is detected or not. If bradycardia is detected, as shown at 91A, then bradycardia pacing is delivered at 92. This cycle continues until bradycardia ceases to be detected, as shown at 91B. A determination is then made as to whether or not tachyarrhythmia has been detected at 93. If tachyarrhythmia is not detected, as shown at 93A, the program will loop back to 91, and there will be no change or delivering of therapy until the detection of either bradycardia or tachyarrhythmia. If tachyarrhythmia is detected, as shown at 93B, then the sensitivity setting is switched to the medium setting at 94 (if not already at that setting).

A decision with respect to tachyarrhythmia confirmation then takes place at 95. If a tachyarrhythmia has been confirmed, as shown at 95A, then antitachyarrhythmia therapy is delivered to the patient, at 96. This antitachyarrhythmia therapy may take the form of defibrillation shock therapy or a train of antitachycardia pacing pulses.

The time limit for the application of antitachyarrhythmia pacing therapy at 96, prior to the delivery of a shock, is of importance. In this regard, reference is made to co-pending U.S. Pat. Application No. 075,629 of Richard Grevis and Loraine Holley, filed July 20, 1987 and entitled "Apparatus and Method for Therapy Adjustment in Implantable Cardioverter", assigned to the assignee of the present invention. In this application, the time limit for application of a shock is determined in accordance with the haemodynamic condition of the patient.

The pacing operation at 96, and more specifically, the manner in which the pacing energy is changed in accordance with events which have occurred, is described in copending U.S. Pat. application Ser. No. 142,535 of Norma Louise Gilli, filed Jan. 11, 1988, entitled "Apparatus and Method for Controlling Pulse Energy in Antitachyarrhythmia and Bradycardia Pacing Device," also assigned to the assignee of the present invention. This application and the one mentioned immediately above are incorporated herein by reference.

On completion of the antitachyarrhythmia therapy, the program executes a low gain subroutine 101, described below with respect to FIG. 5, and then loops back to 94, where sensitivity is set to medium. The program then passes back to 95 for the decision of tachyarrhythmia confirmation.

If there is no confirmation of the tachyarrhythmia at 95, as shown at 95B, then the decision is made at 97 as to whether the condition of asystole is present in the patient. If there is no asystole, as shown at 97A, then the loop passes back to 91 by way of a post therapy delay subroutine 102 described below with respect to FIG. 6, and the cycle starts again with the decision of bradycardia detection and the cycle which follows from there.

If at 97 there appears to be asystole as shown at 97B, it is of importance to realize that this may be due to the absence of a signal when the sensitivity is at the medium setting. The next step is to confirm whether the condition of asystole is, in fact, present. The reason for this is to differentiate between asystole and a fine VF which would not normally produce a signal in the medium sensitivity setting. To achieve differentiation, switching of the sensitivity to the high setting occurs at 98. Following the increase in the sensitivity level, a confirmation of tachyarrhythmia takes place at 99. It is at this time that a differentiation between asystole and a tachyarrhythmia occurs. If the condition is a tachyarrhythmia, as shown at 99A, then antitachyarrhythmia therapy is delivered at 96 in the form of defibrillation shock therapy or antitachycardia pacing. The program then loops back to 94 as previously described.

If there is no confirmation of a tachyarrhythmia at 99, as shown at 99B, then there is either the condition of asystole or the tachyarrhythmia has been reverted At this time, the sensitivity is switched back to the medium setting at 100, and the loop passes back to 91, by way of subroutine 102, for the detection of bradycardia and the cycle as previously described. It is desirable that bradycardia support pacing be inhibited for a programmable period of time after reversion of a tachyarrhythmia to avoid any pro-arrythmic effect Such delay may be implemented in one of timers 47 and 48 or in software, as in subroutine 102, as described below with respect to FIG. 6.

Figure 5:
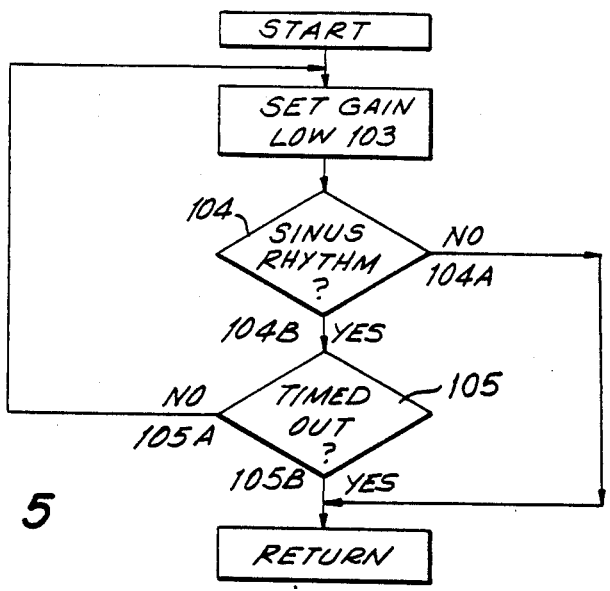
FIG. 5 is a logic flow chart of the low sensitivity subroutine of FIG. 4.

Referring to FIG. 5, in order to distinguish between sinus rhythm and a current of injury T-wave it is necessary to temporarily adjust the detector circuit to a low sensitivity level This is accomplished by the low sensitivity subroutine 101. After the subroutine is accessed and started, the gain is temporarily set low at 103. This low sensitivity setting is lower than the medium sensitivity setting, which in turn, is lower than the high sensitivity setting. Immediately after the gain is set to the low level a determination is made as to whether there is sinus rhythm at 104. If there is no sinus rhythm, the subroutine branches from 104A to RETURN and control is returned to the main program. However, if sinus rhythm is detected (104B), a determination is made at 105 as to whether a predetermined time interval since the delivery of tachyarrhythmia therapy has expired. This time interval may be programmed by the physician to account for the time required in the particular patient for the current of injury T-wave to be diminished to a level at which the detector will not trigger as if it is a QRS complex when the sensitivity is set to the medium level If this time has elapsed (105B), the subroutine is terminated and control is returned to the main program. However, if this time has not elapsed, the subroutine loops from 105A back to 103 where the gain is again set at the low level. As long as sinus rhythm is detected and timeout has not occurred, the gain remains low However, after the timeout occurs the subroutine is terminated and control is transferred back to the program of FIG. 4

Figure 6:
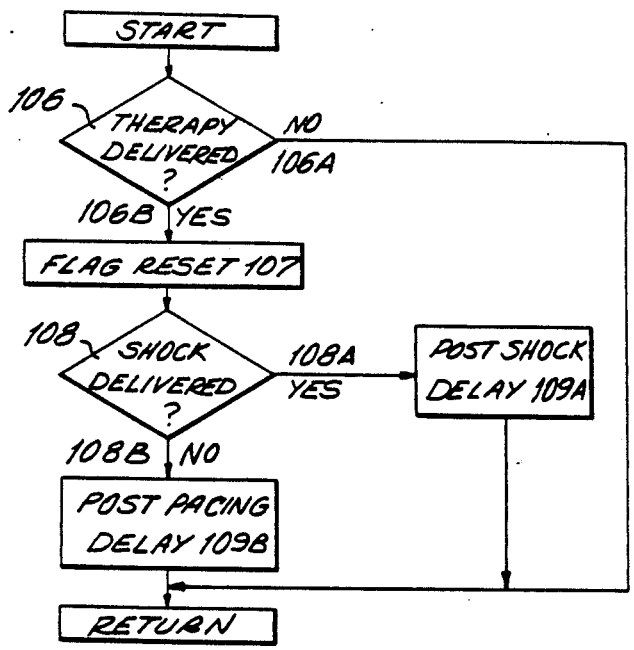
FIG. 6 is a logic flow diagram of the post therapy delay subroutine of FIG. 4.

Referring to FIG. 6, the post therapy delay subroutine 102 is described. Since subroutine 102 is located in the return loop to step 91 for both reversion of a tachyarrhythmia at 97A and for lack of confirmation of a tachyarrhythmia at 99B (FIG. 4), it is necessary that there exist a mode wherein no delay is introduced. Specifically, if a tachyarrhythmia is detected at 93 but there is no confirmation at 95 and apparent asystole at 97 and no confirmation at 99 (even though the sensitivity has been set to the highest level at 98) then a tachyarrhythmia has led directly to asystole. In this case, since no therapy was administered, a delay in pacing is undesirable. Therefore when tachyarrhythmia therapy of any kind is delivered, a flag (not shown in FIG. 4) is set. This flag is read at step 106 to determine whether therapy has been delivered If the answer is NO (106A) then control is immediately returned to the program of FIG. 4 and no delay is introduced. However, if the flag indicates that therapy has been administered, branching to 106B occurs. The flag is reset at 107. At 108 a determination is made as to whether a shock or pacing was last delivered. If the answer to the inquiry at 108 is YES then the program branches at 108A to a post shock delay 109A. After this delay, control is returned to the program of FIG. 4. The length of the post shock delay at 109A is programmable and is typically set so that the time between termination of tachyarrhythmia therapy at 96 and the delivery of bradycardia pacing at 92 is approximately 4.0 seconds. The actual delay introduced at 109A may be just over 2 seconds with the remainder of the delay being generated by low gain subroutine 102 which requires some time to determine whether sinus rhythm is present at 104 (FIG. 5) and bradycardia detection at 91 which typically has a programmed escape or standby interval of approximately 857 ms.

If a shock has not been delivered at 108 then antitachycardia pacing has occurred Subroutine 102 proceeds from 108B to 109B where a post pacing delay is introduced. The length of the post pacing delay is programmable but is generally selected so that the total delay from delivery of tachyarrhythmia pacing at 96 to the delivery of bradycardia pacing at 92 is in the order of 3.0 seconds. Specifically, the post pacing delay introduced at 109B is typically in the order of 1.0 seconds. As is the case for the delay introduced at 109A, the remainder of the delay is made up by the time required to recognize the absence of sinus rhythm at 104 and the escape or standby interval of bradycardia detection at 91.

It will be understood that if sinus rhythm is detected at 104 (FIG. 5) the additional delay of approximately one or two seconds introduced at 109A or 109B will be of little consequence. In this case, if a normal sinus rhythm has been restored, bradycardia will not be detected at 91 and pacing is not delivered in any event. However, should a bradycardia condition commence after the establishment of normal sinus rhythm by the delivery of tachyarrhythmia therapy, the additional delay of one or two seconds will not be critical. If it is desirable to avoid even this delay, the flag set when tachyarrhythmia therapy is delivered at 96 can be reset if normal sinus rhythm is detected at 104.

Figure 7:
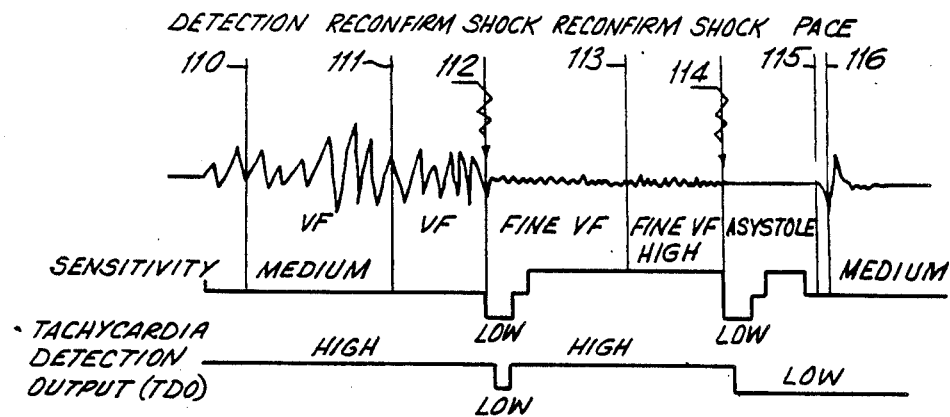
FIG. 7 depicts an ECG trace outlining multiple sensitivity responses to various cardiac conditions and therapies.

Referring to FIG. 7, the ECG trace shows a VF detected at 110, the sensitivity is set at medium and the TDO (tachycardia detection output provided by the algorithms used in microprocessor 16) is high showing a positive response from the medium sensitivity signal.

At 111, there is a reconfirmation of the VF. The reconfirmation is positive (the TDO still shows a high reading) and therefore the sensitivity setting is sufficient and it remains at the medium level.

At 112, a defibrillation shock is given. Immediately post shock 112, low sensitivity subroutine 101 is accessed and the TDO shows a low reading. The sensitivity is then switched from low sensitivity to medium sensitivity (FIG. 4, at 98) and then from medium sensitivity to high sensitivity (FIG. 4, at 94). The high sensitivity then shows a high TDO reading indicating detection of the presence of a fine (low amplitude) VF which was not detected at the low or medium sensitivity levels.

Reconfirmation is given at 113 (FIG. 4, at 99) showing the continued presence of the fine VF, as there is still a high reading on the TDO. Therefore at this stage the high sensitivity level remains in force.

At 114, defibrillation shock therapy is given. Immediately post shock 114, the low sensitivity subroutine 101B is again executed. Since sinus rhythm is not detected, the sensitivity returns to the medium level (FIG. 4, at 94) and then to the high level (FIG. 4, at 98) to pick up any fine VF which may be present. Post shock, the low TDO signal shows the absence or reversion of the VF and the presence of asystole, rather than VF as no waveform is detected at the high sensitivity level. Since the TDO is low at the high sensitivity level, asystole is therefore assumed to be present. VVI pacing treatment is then given at 115.

At 116, sinus rhythm is detected as a result of the pacing therapy, with the sensitivity switched to the medium sensitivity level. It is not necessary to use low sensitivity to distinguish between R-waves and current of injury T-waves in this late occuring sinus rhythm complex.

Figure 8:
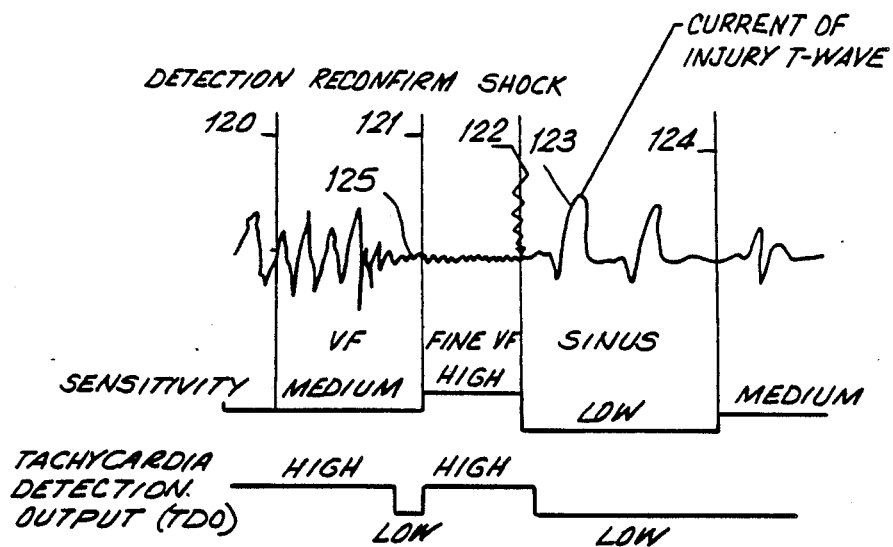
FIG. 8 depicts another ECG trace outlining additional multiple sensitivity responses to various cardiac conditions and therapies.

Referring to FIG. 8, a VF is detected at 120, the sensitivity signal is set at medium sensitivity and a high TDO reading shows that VF is present and that the medium sensitivity setting is sufficient at this stage.

The VF is still present at 121 but has developed into a lower amplitude or fine VF at 125. When this amplitude reduction occurs, the signal is "sub threshold" relative to the medium sensitivity signal. As a result, the TDO switches from high to low. At the reconfirmation point 121, the presence of the low TDO signal triggers a switchover from medium sensitivity level to high sensitivity level. The high sensitivity level picks up the lower amplitude fine VF and a high TDO reading is again generated.

Defibrillation shock therapy is given at 122. Low sensitivity subroutine 101 is accessed immediately post shock. The TDO signal goes low post shock showing the absence of VF, and sinus rhythm is detected at 123. Subroutine 101 then maintains, for the programmed timeout interval at 105, low sensitivity to distinguish R-waves from high amplitude current of injury T-waves.

If the medium sensitivity level were selected at 123, then double sensing of the R and T-waves would occur causing an incorrect reading along with correspondingly incorrect therapy which would cause severe problems and great discomfort to a patient. At 124 when the timeout for low sensitivity has elapsed (FIG. 5, at 105) there is a switchover from low sensitivity to medium sensitivity to pick up the R-waves of the normal sinus rhythm complex. If the duration of the timeout has been properly programmed, by this time the high amplitude current of injury T-wave has gradually decreased in amplitude to a normal amplitude T-wave.

The sensitivity levels in the device which are not variable but are held at fixed, discrete levels during normal operation are programmable by a physician. During programming or patient evaluation, an external programmer (not shown), which communicates with telemetry circuit 38, may be used for switching interchangeably from any one sensitivity level to any other sensitivity level.

Figure 9A:
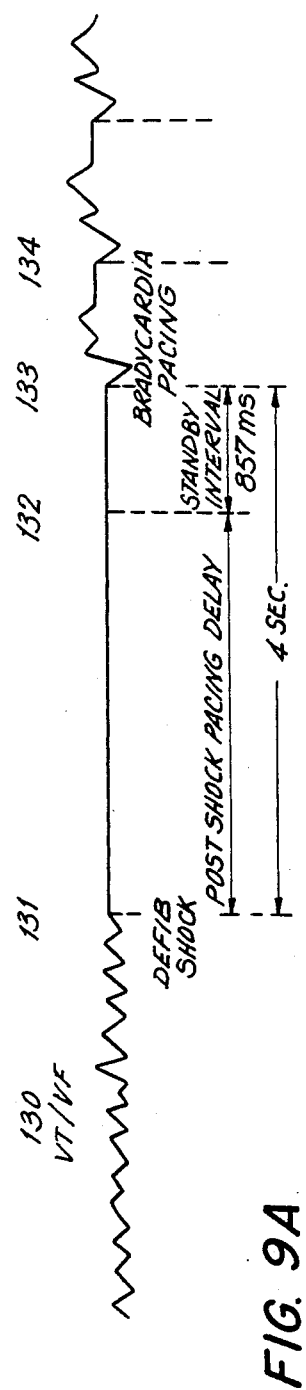
FIG. 9A depicts an ECG trace outlining bradycardia pacing after defibrillation shock with post shock delay.
Figure 9B:
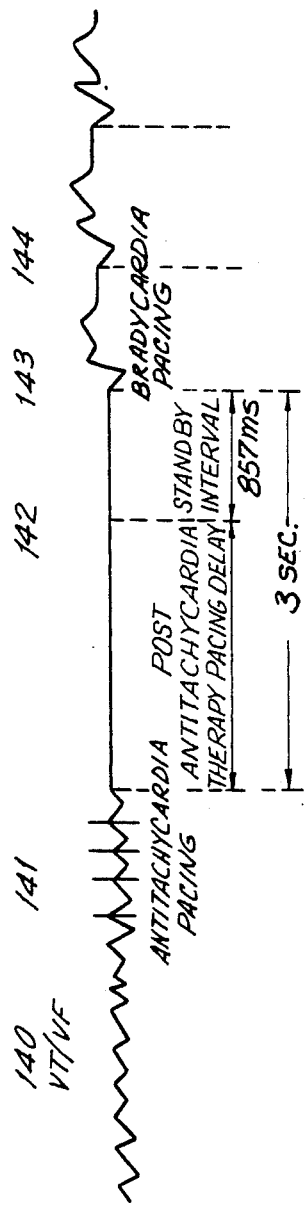
FIG. 9B depicts an ECG trace outlining bradycardia pacing after antitachycardia pacing with post antitachycardia therapy pacing delay.

Referring to FIG. 9A, there is depicted an ECG trace outlining a bradycardia pacing sequence after a defibrillation shock with a post shock pacing delay. At 130, a VT/VF arrhythmia has developed. Defibrillation shock therapy is applied at 131. As shown, the defibrillation shock, which has succeeded in reverting the VT/VF arrhythmia, is followed by a post shock pacing delay interval extending between 131 and 132. At 133, asystole is detected and bradycardia pacing is commenced approximately 4 seconds after the delivery of the defibrillation shock and continues at 134. The proarrhythmic effect of a premature recommencement of bradycardia support pacing immediately post reversion is avoided, as there is sufficient time for the conduction system of the patient's heart to be reorganized and susceptible to bradycardia support pacing Referring to FIG. 9B, there is depicted an ECG trace outlining a bradycardia pacing sequence after antitachycardia pacing with a post therapy pacing delay. At 140, a VT/VF arrhythmia has developed Antitachycardia pacing therapy is applied at 141. As shown, the antitachycardia pacing, which has succeeded in reverting the VT/VF arrhythmia, is followed by a post therapy pacing delay extending from 141 to 142. At 143, asystole is detected and bradycardia pacing is commenced approximately 3 seconds after the termination of antitachycardia pacing and continues at 144. The proarrhythmic effect of a premature recommencement of bradycardia support pacing immediately after reversion has been avoided, as there has been sufficient time for the heart conduction system of the patient to be reorganized and susceptible to bradycardia support pacing.

In the description set forth above, the flow charts of FIG. 4, FIG. 5 and FIG. 6 implement sensitivity adjustment, and post therapy pacing delay It will be recognized that either concept can be used independently of the other; that is an arrythmia control system may have multiple sensitivities without a post therapy delay, although a post therapy delay is preferable Further, post therapy delay may be advantageously used in systems not having multiple sensitivities. For example, post therapy delay may be implemented in the system disclosed in the above-mentioned U.S. Pat. application Ser. No. 142,535 of Norma Louise Gilli, filed Jan. 11, 1988 and entitled "Apparatus and Method for Controlling Pulse Energy in Antitachyarrythmia and Bradycardia Pacing Device."

As noted above, cardiac lead 12 may supply therapy to either the atrium or the ventricle. Thus the apparatus and method of the present invention is suitable for providing antitachyarrhythmia therapy to either the atrium or the ventricle or both.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

We claim:

1. An apparatus for administering electrotherapy to the heart comprising:
    a detector responsive to an electrical signal from the heart, said detector providing an output signal in response to said electrical signal;
    sensitivity control means connected to said detector for controlling the sensitivity of said detector to said electrical signal, said sensitivity control means controlling said sensitivity to a first sensitivity level at a first time;
    tachyarrhythmia detection means for receiving said output signal from said detector set at said first sensitivity level to determine if a tachyarrhythmia is sensed at said first time;
    tachyarrhythmia confirmation means for receiving said output signal from said detector set at said first sensitivity level to confirm the presence of said tachyarrhythmia at a second time after said first time;
    tachyarrhythmia therapy means for delivering tachyarrhythmia therapy to the heart if said tachyarrhythmia confirmation means confirms the presence of tachyarrhythmia at said second time;
    said sensitivity control means controlling said sensitivity of said detector to a second sensitivity level if a tachyarrhythmia is not sensed by said detector at said second time, said second sensitivity level being higher than said first sensitivity level; and
    said tachyarrhythmia therapy means delivering tachyarrhythmia therapy if said detector, at said second sensitivity level, detects tachyarrhythmia.

2. The apparatus of claim 1, wherein said second sensitivity level is sufficient so that said detector provides an output if tachyarrhythmia is present but provides no output during asystole.

3. The apparatus of claim 1, further comprising:
    bradycardia detection means responsive to the output of said detector; and
    bradycardia pacing means for supplying bradycardia pacing to the heart when said bradycardia detecting means detects bradycardia.

4. The apparatus of claim 3, further comprising delay means for delaying delivery of bradycardia pacing pulses by said bradycardia pacing means, after said tachyarrhythmia therapy means delivers tachyarrhythmia therapy.

5. The apparatus of claim 4, wherein said delay means delays said delivery of bradycardia therapy for a predetermined time interval.

6. The apparatus of claim 5, further comprising programming means connected to said delay means for programming said predetermined time interval.

7. The apparatus of claim 4, wherein said tachyarrhythmia therapy means delivers a first kind of tachyarrhythmia therapy and a second kind of tachyarrythmia therapy, said delay means having a first delay interval generation means for delay after said first kind of therapy, and a second delay, interval generation means for delay after said second kind of therapy.

8. The apparatus of claim 7, wherein delay of said first delay interval generation means and of said second delay interval generation means are independently programmable.

9. The apparatus of claim 1, wherein said sensitivity control means controls said sensitivity to change from said second sensitivity level to said first sensitivity level when said tachyarrhythmia detection means fails to detect a tachyarrhythmia when said detector is at said second sensitivity level.

10. The apparatus of claim 9, further comprising:
    bradycardia detection means responsive to the output of said detector, when said sensitivity control means controls said detector sensitivity to return to said first sensitivity level; and
    bradycardia pacing means for supplying bradycardia pacing when said bradycardia detection means detects bradycardia.

11. The apparatus of claim 1, wherein said tachyarrhythmia therapy means includes at least one of:
    a tachyarrhythmia pacing means, and
    a cardioversion means.

12. The apparatus of claim 1, further comprising programming means operatively connected to said sensitivity control means for programming at least one of said first sensitivity level and said second sensitivity level.

13. The apparatus of claim 1, wherein after tachyarrhythmia therapy has been delivered to the heart by said tachyarrhythmia therapy means, said sensitivity control means controls the sensitivity of said detector to a third level, said third sensitivity level being of lower sensitivity than said first level.

14. The apparatus of claim 13, wherein said third sensitivity level is sufficiently high so that said detector detects sinus rhythm, but is sufficiently low so that said detector does not detect a current of injury T-wave.

15. The apparatus of claim 13, wherein said sensitivity control means controls said sensitivity to said third level for at least a period of time sufficient to detect the presence of sinus rhythm.

16. The apparatus of claim 15, wherein if sinus rhythm is not detected at said third sensitivity level, said sensitivity control means controls the sensitivity of said detector to change from said third sensitivity level to said second sensitivity level.

17. The apparatus of claim 15, wherein said period of time is predetermined.

18. The apparatus of claim 15, further comprising programing means operative connected to said sensitivity control means for programming duration of said period of time.

19. The apparatus of claim 13, further comprising sensitivity programming means for programming at least one of said first sensitivity level, said second sensitivity level and said third sensitivity level.

20. The apparatus of claim 13, further comprising sensitivity programming means for independently programming at least one of said first sensitivity level, said second sensitivity level and said third sensitivity level.

21. An apparatus for treating tachyarrhythmias comprising: sensing means for sensing the presence of a patient tachyarrhythmia, tachyarrhythmia therapy delivery means for delivering tachyarrhythmia therapy, programming means for programming at least two sensitivity levels, a detector means programmable to said sensitivity levels for producing output signals at each of said sensitivity levels, a first sensitivity level being for sensing of sinus, VF and VT, and a second sensitivity level being a higher level of sensitivity than said first sensitivity level, said second sensitivity level being for differentiating VF not detected at said first sensitivity level from an asystole condition, and switching means for switching from said first sensitivity level to said second sensitivity, level when there is an absence of output signals from said detector means at the first sensitivity level.

22. The apparatus of claim 21, wherein said switching means switches back to the first sensitivity level following the delivery of one of tachyarrhythmia therapy, a sensed sinus event and a paced event.

23. The apparatus of claim 21, wherein said programming means also programs third sensitivity level for distinguishing between (a) post-therapy R-waves and (b) current of injury T-waves and far field R-waves.

24. A medical device as claimed in claim 23, wherein said switching means switches interchangeably to and from said third sensitivity level.

25. A method for administering electrotherapy to the heart comprising the steps of:
setting the sensitivity of a detector to an electrical signal from the heart to a first sensitivity level;
detecting the presence of a tachyarrhythmia with said detector, at a first time;
determining whether said tachyarrhythmia is detected by said detector at a second time, at said first sensitivity level, said second time being after said first time;
delivering tachyarrhythmia therapy if said tachyarrhythmia is detected at said second time;
changing said sensitivity to a second sensitivity level if said tachyarrhythmia is not detected at said second time, said second sensitivity level being higher than said first sensitivity level;
determining whether said tachyarrhythmia is detected at said second sensitivity level at a third time, said third time being later than said second time; and
delivering tachyarrhythmia therapy if said tachyarrhythmia is detected at said third time.

26. The method of claim 25, further comprising the step of:
changing said sensitivity back to said first sensitivity level if said tachyarrhythmia is not detected at said third time.

27. The method of claim 26, further comprising the steps of:
detecting the presence of bradycardia after said step of changing said sensitivity back to said second level, and
delivering bradycardia pacing when bradycardia is detected 28. The method of claim 27, further comprising the step of delaying the delivering of bradycardia pacing by a predetermined period of time after delivery of said tachyarrhythmia therapy 29. The method of claim 28, wherein said tachyarrhythmia therapy is of a first type of therapy and a second type of therapy, said first type of therapy being delayed for a first delay interval and said second type of therapy being delayed for a second delay interval.

30. The method of claim 29, further comprising the step of independently programming said first delay interval and said second delay interval.

31. The method of claim 28, further comprising the step of programming said predetermined period of time.

32. The method of claim 25, wherein said tachyarrhythmia therapy includes at least one of pacing and cardioversion.

33. The method of claim 25, further comprising the step of programming at least one of said first sensitivity level and said second sensitivity level.

34. The method of claim 25, wherein at least one of said first sensitivity level and said second sensitivity level is programmed to a fixed level.

35. The method of claim 25, further comprising the steps of:
setting said sensitivity of said detector to a third level after the delivery of tachyarrhythmia therapy, for a period of time sufficient to detect the presence of sinus rhythm, said third level being lower than said first level;
determining whether sinus rhythm is detected by said detector at said third sensitivity level;
maintaining said sensitivity at said third level for a predetermined period of time if sinus rhythm is detected; and
changing said sensitivity to said second level if sinus rhythm is not detected.

36. The method of claim 35, wherein said third sensitivity level is sufficiently high to detect sinus rhythm and insufficiently high to detect a current of injury T-wave.

37. The method of claim 35, further comprising the step of programming said first sensitivity level, said second sensitivity level and said third sensitivity level.

38. The method of claim 35, further comprising the step of independently programming said first sensitivity level, said second sensitivity level and said third sensitivity level.

39. The method of claim 35, further comprising the step of programming a duration of said predetermined period of time.

* * * * *